US011110452B2

(12) United States Patent
Fisher et al.

(10) Patent No.: US 11,110,452 B2
(45) Date of Patent: Sep. 7, 2021

(54) MULTILAYER FLUIDIC DEVICES AND METHODS FOR THEIR FABRICATION

(71) Applicant: Illumina, Inc., San Diego, CA (US)

(72) Inventors: Jeffrey S. Fisher, San Diego, CA (US); John A. Moon, San Diego, CA (US); Bala Murali Venkatesan, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 390 days.

(21) Appl. No.: 16/026,847

(22) Filed: Jul. 3, 2018

(65) Prior Publication Data
US 2019/0001328 A1    Jan. 3, 2019

Related U.S. Application Data

(63) Continuation of application No. 15/902,590, filed on Feb. 22, 2018, now Pat. No. 10,807,089, which is a
(Continued)

(51) Int. Cl.
*B01L 3/00*          (2006.01)
*B81C 1/00*          (2006.01)
(Continued)

(52) U.S. Cl.
CPC .... *B01L 3/502707* (2013.01); *B29C 65/1435* (2013.01); *B29C 65/1467* (2013.01);
(Continued)

(58) Field of Classification Search
CPC ....... B01L 3/502707; B01L 2200/0689; B01L 2300/0645; B01L 2300/0816;
(Continued)

(56) References Cited

U.S. PATENT DOCUMENTS

| | | | |
|---|---|---|---|
| 5,130,238 | A | 7/1992 | Malek et al. |
| 5,455,166 | A | 10/1995 | Walker |

(Continued)

FOREIGN PATENT DOCUMENTS

| | | |
|---|---|---|
| DE | 102004033440 | 2/2006 |
| FR | 2856047 | 12/2007 |

(Continued)

OTHER PUBLICATIONS

International Search Report and Written Opinion, "Application No. PCT/US2013/030940", dated Nov. 19, 2013, 4 pages.
(Continued)

*Primary Examiner* — Lore R Jarrett
(74) *Attorney, Agent, or Firm* — Illumina, Inc.

(57) ABSTRACT

A method of making a flowcell includes bonding a first surface of an organic solid support to a surface of a first inorganic solid support via a first bonding layer, wherein the organic solid support includes a plurality of elongated cutouts. The method further includes bonding a surface of a second inorganic solid support to a second surface of the organic solid support via a second bonding layer, so as to form the flowcell. The formed flowcell includes a plurality of channels defined by the surface of the first inorganic solid support, the surface of the second inorganic solid support, and walls of the elongated cutouts.

19 Claims, 5 Drawing Sheets

Related U.S. Application Data continuation of application No. 14/774,919, filed as application No. PCT/US2013/030940 on Mar. 13, 2013, now abandoned.

(51) Int. Cl.

| | | |
|---|---|---|
| *B29C 65/14* | (2006.01) | |
| *B29C 65/16* | (2006.01) | |
| *B29C 65/00* | (2006.01) | |
| *B81C 3/00* | (2006.01) | |
| *C12Q 1/6874* | (2018.01) | |
| *B29K 507/04* | (2006.01) | |
| *B29C 65/82* | (2006.01) | |
| *B29L 31/00* | (2006.01) | |
| *B29L 9/00* | (2006.01) | |
| *B29L 31/34* | (2006.01) | |

(52) U.S. Cl.
CPC ...... *B29C 65/1477* (2013.01); *B29C 65/1483* (2013.01); *B29C 65/1635* (2013.01); *B29C 65/1677* (2013.01); *B29C 65/1683* (2013.01); *B29C 66/112* (2013.01); *B29C 66/114* (2013.01); *B29C 66/1122* (2013.01); *B29C 66/45* (2013.01); *B29C 66/53461* (2013.01); *B29C 66/71* (2013.01); *B29C 66/72326* (2013.01); *B29C 66/739* (2013.01); *B29C 66/746* (2013.01); *B29C 66/7465* (2013.01); *B81C 1/00071* (2013.01); *B81C 3/001* (2013.01); *C12Q 1/6874* (2013.01); B01L 2200/0689 (2013.01); B01L 2200/12 (2013.01); B01L 2300/0645 (2013.01); B01L 2300/0816 (2013.01); B01L 2300/0877 (2013.01); B01L 2300/0887 (2013.01); B01L 2300/12 (2013.01); B29C 65/1409 (2013.01); B29C 65/1606 (2013.01); B29C 65/1609 (2013.01); B29C 65/1612 (2013.01); B29C 65/1654 (2013.01); B29C 65/8223 (2013.01); B29C 65/8246 (2013.01); B29C 66/026 (2013.01); B29C 66/028 (2013.01); B29C 66/72321 (2013.01); B29C 66/72325 (2013.01); B29C 66/7392 (2013.01); B29C 66/7394 (2013.01); B29K 2507/04 (2013.01); B29L 2009/005 (2013.01); B29L 2031/34 (2013.01); B29L 2031/756 (2013.01); B81B 2201/058 (2013.01); B81C 2201/019 (2013.01); B81C 2203/035 (2013.01)

(58) Field of Classification Search
CPC ......... B01L 2300/0877; B01L 2200/12; B01L 2300/0887; B01L 2300/12; B29C 66/7394; B29C 65/1606; B29C 65/1609; B29C 65/1612; B29C 65/1654; B29C 65/8223; B29C 65/8246; B29C 66/026; B29C 66/028; B29C 66/7392; B29C 65/1409; B29C 66/72326; B29C 66/739; B29C 65/1435; B29C 65/1467; B29C 65/1477; B29C 65/1483; B29C 65/1635; B29C 65/1677; B29C 65/1683; B29C 66/112; B29C 66/1122; B29C 66/114; B29C 66/45; B29C 66/53461; B29C 66/71; B29C 66/7465; B29C 66/746; B29C 66/72325; B29C 66/72321; B29C 66/7934; C12Q 1/6874; B81C 2203/035; B81C 2201/019; B81C 1/00071; B81B 2201/058; B29K 2507/04; B29L 2031/756; B29L 2009/005; B29L 2031/34

See application file for complete search history.

(56) References Cited

U.S. PATENT DOCUMENTS

| | | |
|---|---|---|
| 5,599,675 A | 2/1997 | Brenner |
| 5,641,658 A | 6/1997 | Adams et al. |
| 5,750,341 A | 5/1998 | MacEvicz |
| 6,210,891 B1 | 4/2001 | Nyren et al. |
| 6,214,587 B1 | 4/2001 | Dattagupta |
| 6,258,568 B1 | 7/2001 | Nyren |
| 6,266,459 B1 | 7/2001 | Walt et al. |
| 6,274,320 B1 | 8/2001 | Rothberg et al. |
| 6,355,431 B1 | 3/2002 | Chee et al. |
| 6,770,441 B2 | 8/2004 | Dickinson et al. |
| 6,859,570 B2 | 2/2005 | Walt et al. |
| 6,877,892 B2 | 4/2005 | Karp |
| 6,890,741 B2 | 5/2005 | Fan et al. |
| 6,913,884 B2 | 7/2005 | Stuelpnagel et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,582,420 B2 | 9/2009 | Oliphant et al. |
| 2002/0055100 A1 | 5/2002 | Kawashima et al. |
| 2002/0102578 A1* | 8/2002 | Dickinson .......... G01N 21/6452 435/6.11 |
| 2003/0138973 A1 | 7/2003 | Wagner |
| 2004/0002090 A1 | 1/2004 | Mayer et al. |
| 2004/0026023 A1 | 2/2004 | DeMeter |
| 2004/0096853 A1 | 5/2004 | Mayer |
| 2005/0053980 A1 | 3/2005 | Gunderson et al. |
| 2005/0181440 A1 | 8/2005 | Chee et al. |
| 2006/0030035 A1 | 2/2006 | Joseph et al. |
| 2006/0124230 A1 | 6/2006 | Chartier |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2009/0186349 A1 | 7/2009 | Gunderson et al. |
| 2010/0047790 A1 | 2/2010 | Southern et al. |
| 2010/0104480 A1 | 4/2010 | Viovy et al. |
| 2010/0111768 A1* | 5/2010 | Banerjee .............. C12Q 1/6869 422/82.08 |
| 2010/0137143 A1 | 6/2010 | Rothberg et al. |
| 2010/0282617 A1 | 11/2010 | Rothberg |
| 2011/0059865 A1 | 3/2011 | Smith et al. |
| 2011/0105356 A1 | 5/2011 | Derosier et al. |
| 2011/0122406 A1 | 5/2011 | Khine et al. |
| 2011/0266362 A1 | 11/2011 | Ciampini et al. |
| 2012/0006783 A1 | 1/2012 | Pouydebasque et al. |
| 2012/0009099 A1 | 1/2012 | Lin |
| 2012/0316086 A1 | 12/2012 | Lin et al. |
| 2013/0037207 A1 | 2/2013 | Yamamoto et al. |
| 2013/0116153 A1 | 5/2013 | Bowen et al. |
| 2013/0338042 A1 | 12/2013 | Shen et al. |
| 2014/0079923 A1 | 3/2014 | George et al. |
| 2014/0243224 A1 | 8/2014 | Barnard et al. |

FOREIGN PATENT DOCUMENTS

| | | |
|---|---|---|
| JP | 2008284782 | 11/2008 |
| WO | 1989/10977 A1 | 11/1989 |
| WO | 1991/006678 A1 | 5/1991 |
| WO | 2000/063437 A2 | 10/2000 |
| WO | 2004/018497 A2 | 3/2004 |
| WO | 2006/046164 | 5/2006 |

(56) References Cited

FOREIGN PATENT DOCUMENTS

| WO | 2007/123744 | A2 | 11/2007 |
|----|-------------|----|---------|
| WO | 2008/093098 | A2 | 8/2008  |

OTHER PUBLICATIONS

Bains, et al., "A novel method for nucleic acid sequence determination", J. Theor Biol., 135(3), 1988, 303-307.

Bentley, et al., "Accurate whole human genome sequencing using reversible terminator chemistry", Nature, vol. 456, 2008, 53-59.

Dean, et al., "Comprehensive human genome amplification using multiple displacement amplification", Proc. Natl. Acad. Sci. USA 99, 2002, 5261-5266.

Drmanac, et al., "Accurate sequencing by hybridization for DNA diagnostics and individual genomics", Nature Biotechnology, 1998, 54-58.

Fodor, et al., "Light-Directed, Spatially Addressable Parallel Chemical Synthesis", Science, vol. 251, 1991, 767-773.

Korlach, et al., "Selective aluminum passivation for targeted immobilization of single DNA polymerase molecules in zero-mode waveguide nanostructures", PNAS, vol. 105, No. 4, 2008, 1176-1181.

Lage, et al., "Whole genome analysis of genetic alterations in small DNA samples using hyperbranched strand displacement amplification and array-CGH", Genome Res., 2003, 294-307.

Levene, et al., "Zero-Mode Waveguides for Single-Molecule Analysis at high concentrations", Science 299, 2003, 682-686.

Lizardi, "Mutation detection and single-molecule counting using isothermal rolling-circle amplification", Nature Genetics, vol. 19, 1998, 225-232.

Lundquist, et al., "Parallel confocal detection of single molecules in real time", Opt. Lett. 33(9), 2008, 1026-1028.

Ronaghi, M., et al., "A Sequencing Method Based on Real-Time Pyrophosphate", Science 281 (5375), Jul. 17, 1998, 363-365.

Ronaghi, M., "Pyrosequencing sheds light on DNA sequencing", Genome Res, 11(1), 2001, 3-11.

Ronaghi, M., et al., "Real-time DNA sequencing using detection of pyrophosphate release", Anal. Biochem. Nov. 1, 1996; 242(1): 84-9.

Shendure, et al., "Accurate Multiplex Polony Sequencing of an Evolved Bacterial Genome", Science, Sep. 9, 2005, 1728-1732.

Walker, et al., "A Chemiluminescent DNA Probe Test Based on Strand Displacement Amplification", Molecular Methods for Virus Detection, 1995, Academic Press Inc., Ch 15 pp. 329-349., 1995.

Walker, et al., "Strand displacement amplification—an isothermal, in vitro DNA amplification technique", Nucleic Acids Res., 1992, 1691-1696.

* cited by examiner

MULTILAYER FLUIDIC DEVICES AND METHODS FOR THEIR FABRICATION

CROSS-REFERENCE TO RELATED APPLICATIONS

This application is a continuation of U.S. Ser. No. 15/902,590, filed Feb. 22, 2018, which is itself a continuation of U.S. Ser. No. 14/774,919, filed Sep. 11, 2015, which is itself a national stage entry under 35 U.S.C. § 371 of PCT/US2013/030940, filed Mar. 13, 2013, each of which is incorporated by reference herein in its entirety.

BACKGROUND

This disclosure relates generally to fluidic devices used for analytical and synthetic chemistry, and more specifically to flowcells used for sequencing and other analyses of nucleic acid arrays.

Biological arrays have become a key tool for genomic analysis in research settings and are poised to become important tools in clinical settings for diagnosing human disease. In certain applications, individual DNA probes are attached to a geometric grid on an array support. A test sample, such as from a known person or organism, is exposed to the grid, such that complimentary gene fragments bind to probes at known locations on the array. Alternatively, a test sample, such as from a known person or organism, can be attached to the support and evaluated, for example, using a DNA sequencing technique. In either format the array can be detected, for example, using fluorescent reagents delivered fluidically to the array surface. Often the techniques utilize multiple steps of fluid delivery and multiple detection steps. The need for precise fluidic manipulations and accurate high-resolution detection in array techniques places big demands on arrays, the materials from which they are made and the devices that house them.

Significant improvements have recently been made in the biochemical assays that are run on arrays, the imaging systems used to detect the arrays and the data processing systems used to evaluate the results obtained from the arrays. For example, improvements in sequencing chemistry, imaging optics and sequence data analysis used in commercial sequencing platforms have resulted in faster, more accurate and higher resolution genomic analysis than ever before. However, as these improvements occur, the resulting increase in sequence platform usage creates increased demand for arrays and the flowcells that house them. Because arrays and flowcells are generally disposable, this demand scales directly with the increased demand for genomic analysis. Improvements in array and flowcell fabrication are needed to prevent the cost of their production from becoming an impediment to reductions in the overall cost of genomic analyses. Furthermore, improvements in array and flowcell fabrication are also needed to avoid counteracting the advances in other components of genetic analysis platforms that are otherwise positioning the technology to become more clinically useful and widespread. The present invention satisfies these needs and provides other advantages as well.

BRIEF SUMMARY

The present disclosure provides a fluidic device including (a) an inorganic solid support attached to an organic solid support by a bonding layer, wherein the inorganic solid support has a rigid structure and wherein the bonding layer includes a material that absorbs radiation at a wavelength that is transmitted by the inorganic solid support or the organic solid support, and (b) at least one channel formed by the attachment of the inorganic solid support to the organic solid support, wherein the channel is configured to contain a liquid and the bonding layer that attaches the inorganic solid support to the organic solid support provides a seal against liquid flow. In particular embodiments, the material that absorbs the radiation is not an electrically conductive material such as a metal.

This disclosure further provides a method for making a multilayer device. The method can include the steps of (a) providing an inorganic solid support and an organic solid support, wherein the inorganic solid support has a rigid structure; (b) providing a radiation-absorbing material; (c) contacting the inorganic solid support, the organic solid support and the radiation-absorbing material in a configuration wherein the radiation-absorbing material is present at an interface between the inorganic solid support and the organic solid support; and (d) applying compression at the interface and irradiating the radiation-absorbing material with the radiation to form a bonding layer between the inorganic solid support and the organic solid support. In particular embodiments, the radiation-absorbing material is not an electrically conductive material such as a metal.

Also provided is a fluidic device having at least one channel defined by an inorganic solid support attached to an organic solid support by a bonding layer, wherein the fluidic device is made by the process of: (a) contacting the inorganic solid support, the organic solid support and a radiation-absorbing material in a configuration wherein the radiation-absorbing material is present at an interface between the inorganic solid support and the organic solid support; and (b) applying compression at the interface and irradiating the radiation-absorbing material with the radiation to form the bonding layer between the inorganic solid support and the organic solid support. In particular embodiments, the radiation-absorbing material is not an electrically conductive material such as a metal.

DETAILED DESCRIPTION

Terms used herein will be understood to take on their ordinary meaning in the relevant art unless specified otherwise. Several terms used herein and their meanings are set forth below.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, electrodes on a substrate, metal pads on a substrate, gel pads on a substrate, ridges on a substrate or channels in a substrate. The sites of an array can be separate substrates each bearing a different molecule. Different molecules attached to separate substrates can be identified according to the locations of the substrates on a surface to which the substrates are associated. Exemplary arrays in which separate substrates are located on a surface include, without limitation, those having beads in wells.

As used herein, the term "bonding layer" refers to an area that attaches two support structures to each other. For example, the bonding layer can include one or more covalent or non-covalent bonds that form the attachment. A covalent bond is characterized by the sharing of pairs of electrons between atoms. A chain of two or more covalent bonds can form a molecular link between two support structures. Thus, the bonding layer can have a thickness of one or more covalent bond-lengths. In particular embodiments, each molecular link can span the bonding layer uninterrupted by any non-covalent bonds. Alternatively, a molecular link can include one or more non-covalent bonds in a chain of bonds that span the bonding layer. A non-covalent bond is a chemical bond that does not involve the sharing of pairs of electrons and can include, for example, hydrogen bonds, ionic bonds, van der Waals forces, hydrophilic interactions and hydrophobic interactions. In at least some embodiments, the bonding layer can include a combination of covalent molecular links that span the bonding layer and non-covalent linkages that span at least part of the bonding area. Any of a variety of materials that join, fasten, adhere, connect or bind the solid supports can be included in a bonding layer. Preferably a bonding layer prevents fluid leakage by forming a seal.

As used herein, the term "channel" refers to an elongated passage that is configured to contain a fluid or direct the flow of a fluid in or on a solid support. An example is an open channel configured as a groove, trench, straight, furrow or the like. The transverse cross section of an open channel can be, for example, U-shaped, V-shaped, curved, angular, polygonal, or hyperbolic. Another example is a closed channel configured as a pipe, tube, tunnel or the like. A closed channel can have a circular, elliptical, square, rectangular, or polygonal cross section.

As used herein, the term "chemically reactive layer" refers to a surface coating or region between surfaces that contains at least one moiety that is capable of becoming covalently modified or covalently attached to at least one other moiety upon physical or chemical stimulation. In some embodiments the region between the surfaces can be occupied by a liquid, gas, solid or plasma that contains the reactive moiety.

As used herein, the term "compression" refers to a force that brings two objects together. For example, two solid supports can be brought together by clamping the supports to each other, pressing the two supports together, placing one support atop another in a gravitational field (e.g. under earth's gravity or centrifugally induced gravity) or the like.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "gel" refers to a semi-rigid material that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, U.S. patent application Ser. No. 13/784, 368, which is incorporated herein by reference). Particularly useful gel material will conform to the shape of a surface, for example, to enter pits, wells, or other concave features on the surface.

As used herein, the term "inorganic solid support" refers to a substrate having an internal structure held together by bonds between inorganic atoms. An inorganic solid support can, however, have an organic layer on the surface of the substrate. A trace or small amount of organic matter can occur in the internal structure of the inorganic solid support so long as the structural integrity is primarily mediated by bonds and interactions between inorganic atoms. Exemplary inorganic solid supports include, but are not limited to, glass and modified or functionalized glass, ceramics, silica or silica-based materials including silicon and modified silicon, metals, and optical fiber bundles.

As used herein, the term "interface" refers to a region at the boundary of two materials. For example, the term can refer to an area between two solid supports, between a solid support and a chemically reactive layer, between chemically reactive layers on two solid supports, between a bonding layer and a solid support, etc. The term can further refer to the surface of one or both of the materials that occur at the boundary. For example, the term can refer to a layer that is present on the surface of one or both materials.

As used herein, the term "organic solid support" refers to a substrate having an internal structure that is held together by bonding between organic atoms or molecules. An organic solid support can, however, have one or more inorganic atoms in the internal structure or on the surface of the substrate. For example, a trace or small amount of inorganic matter can occur in the internal structure of the organic solid support. Exemplary materials for organic solid supports include, but are not limited to, plastics, thermoplastics, thermosets, nylon, cyclic olefin copolymers (e.g. Zeonor), cyclic olefin polymers, carbon fiber, and polymers. Exemplary thermoplastics include polyacrylate, polyamide, polyimide (e.g. Kapton products from DuPont), polybutylene terephthalate, polycarbonate, polyether ketone, polyethylene, polyphenylene sulfide, polyacetal, polypropylene, polystyrene, polysulfone, polyvinyl butyral and polyvinyl chloride. Thermoplastics are particularly useful of which Kapton KJ and black Kapton KJ are examples.

As used herein, the term "planar surface" refers to an external part or external layer of a solid support that is apparently flat. Flatness can be apparent to the naked eye or at a magnification level of at most 5×, 10×, 100×, or 1000×. The planar surface can be on a portion of a substrate that otherwise has features such as wells, pits, metal features, gel features, channels, ridges, raised regions, pegs, posts or the like.

As used herein, the term "rigid structure" refers to a substrate that is stiff or inflexible. The rigid structure can optionally be capable of taking up a liquid (e.g. due to porosity) but will typically not swell substantially when taking up the liquid and will not contract substantially when the liquid is removed by drying.

As used herein, the term "solid support" refers to a substrate that is insoluble in aqueous liquid. The substrate can be non-porous or porous. The solid support can be rigid or flexible. A nonporous solid support is generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments have at least one surface located within a flowcell apparatus. Exemplary flowcells are set forth in further detail below.

The embodiments set forth below and recited in the claims can be understood in view of the above definitions.

This disclosure provides a method for making a multilayer device. The method can include the steps of (a) providing an inorganic solid support and an organic solid support, wherein the inorganic solid support has a rigid structure; (b) providing a radiation-absorbing material; (c) contacting the inorganic solid support, the organic solid support and the radiation-absorbing material in a configuration wherein the radiation-absorbing material is present at an interface between the inorganic solid support and the organic solid support; and (d) applying compression at the interface and irradiating the radiation-absorbing material with the radiation to form a bonding layer between the inorganic solid support and the organic solid support. In particular embodiments, the radiation-absorbing material is not an electrically conductive material. For example, in some embodiments, the radiation-absorbing material is not a metal.

In some embodiments, the above method can be used to create a device with open channels, reservoirs or other features. Optionally, a device can be fabricated to have channels, reservoirs or other features that are enclosed. For example, the method for making a multilayer device can, optionally, further include the steps of (e) providing a second inorganic solid support; (f) contacting the second inorganic solid support with the organic solid support in a configuration wherein the radiation-absorbing material is present at a second interface between the second inorganic solid support and the organic solid support; and (g) applying compression at the second interface and irradiating the radiation-absorbing material with the radiation to form a bonding layer between the second inorganic solid support and the organic solid support. Whether or not the device includes enclosed features, steps (e) through (g) can be carried out once or more to create several spaced layers (i.e. multiple multilayers) each having an organic solid support sandwiched between two inorganic solid supports.

Figure 2:
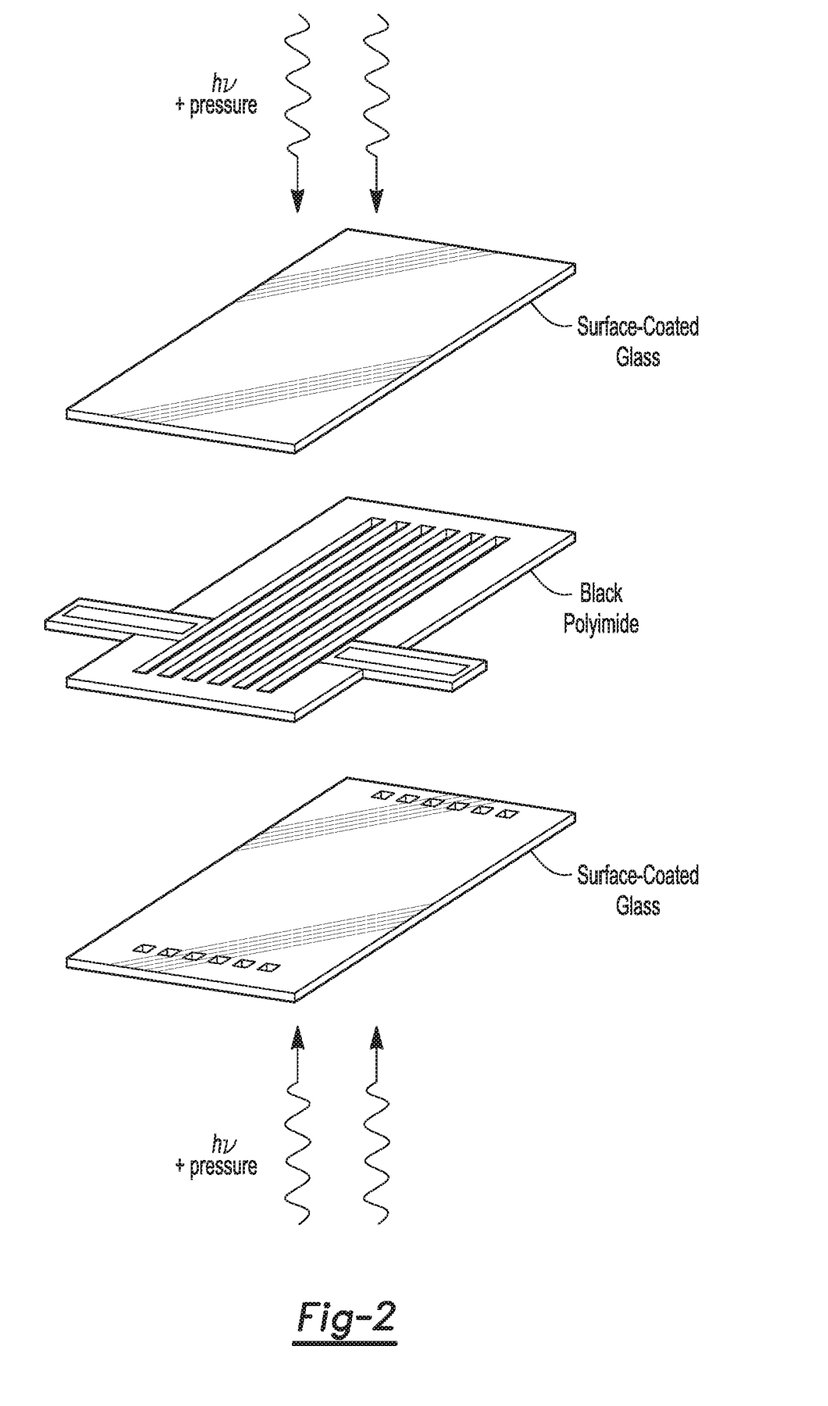
FIG. 2 shows a diagrammatic representation of a process for fabricating a multilayer flowcell.
Figure 4:
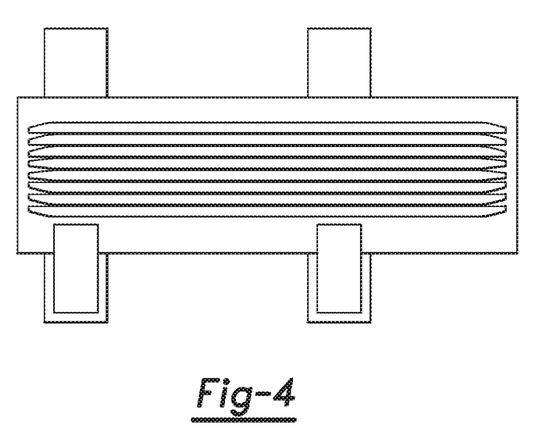
FIG. 4 shows a photograph of a flowcell having top and bottom surfaces with ITO layers that are each connected to a pair of electrical contacts.

The methods set forth herein are useful for fabricating devices having a variety of configurations and dimensions. For example, the devices can have planar layers that are stacked to form planar structures, such as those commonly characterized as chips, slides, cartridges and the like. Examples of devices having a generally planar structure are shown in FIG. 2 and FIG. 4. Non-planar devices can also be fabricated using the methods set forth herein. The layers can be non-planar being instead, for example, curved as is found for structures that are tubular, cylindrical, conical or spherical. A multilayer device can have a combination of planar and non-planar regions. For example a generally planar support can have curved features such as wells, channels, pits, indents, pillars, protuberances and the like. Thus some of the layers in a multilayer device or used to make a multilayer device can be planar whereas other layers are non-planar.

The dimensions of a device made in accordance with the methods set forth herein can be on any of a variety of scales. For example, devices of the present disclosure may have outer dimensions in the range of a few meters, 1 to 100 centimeters, 1-1000 millimeters, 1-1000 micrometers, or 1-1000 nanometers. Larger or smaller dimensions are also possible. For example, in some embodiments devices of the present disclosure have outer dimensions with an area that is no larger than $1 \text{ m}^2$, $10 \text{ cm}^2$, $1 \text{ cm}^2$, $100 \text{ mm}^2$, $10 \text{ mm}^2$, $\text{mm}^2$, $100 \text{ }\mu\text{m}^2$, $10 \text{ }\mu\text{m}^2$, $1 \text{ }\mu\text{m}^2$, $100 \text{ nm}^2$, $10 \text{ nm}^2$, $1 \text{ nm}^2$, or smaller. Alternatively or additionally, devices of the present disclosure have outer dimensions with an area that is at least $1 \text{ nm}^2$, $10 \text{ nm}^2$, $100 \text{ nm}^2$, $1 \text{ }\mu\text{m}^2$, $10 \text{ }\mu\text{m}^2$, $100 \text{ }\mu\text{m}^2$, $1 \text{ mm}^2$, $10 \text{ mm}^2$, $100 \text{ mm}^2$, $1 \text{ cm}^2$, $10 \text{ cm}^2$, $1 \text{ m}^2$ or more.

The thickness of a device provided by the present disclosure will follow, at least in part, from the thickness of the layers present in the device. Different layers can have different thickness based on desired properties or uses. For example, an inorganic solid support may provide desired structural support, rigidity, flexibility, optical properties, thermal transfer properties or the like, each of which can be influenced by thickness of the material. Similarly, it may be desired that an organic solid support have one or more of these properties. As exemplified by some embodiments herein, an organic solid support may function as a spacer. When used in a fluidic device the thickness of the spacer can influence the volume of channels or other fluidic features of the device. The thickness of a solid support or individual layer present in a multilayer device or used in a method of making a multilayer device can be, for example, at least 1 nm, 10 nm, 100 nm, 1 µm, 10 µm, 100 µm, 1 mm, 10 mm, 100 mm, 1 cm, 10 cm, 1 m or more. Alternatively or additionally, the thickness of a solid support or other layer may be no larger than 1 µm, 10 cm, 1 cm, 100 mm, 10 mm, 1 mm, 100 µm, 10 µm, 1 µm, 100 nm, 10 nm, 1 nm, or smaller.

Accordingly, the volume of space occupied by a multilayer device or layer of a multilayer device can be in a range that is at least $1 \text{ }\mu\text{m}^3$, $10 \text{ }\mu\text{m}^3$, $100 \text{ }\mu\text{m}^3$, $1 \text{ mm}^3$, $10 \text{ mm}^3$, $100 \text{ mm}^3$, $1 \text{ cm}^3$, $10 \text{ cm}^3$, $1 \text{ m}^3$, several $\text{m}^3$ or larger. Alternatively or additionally, the volume of space occupied by a multilayer device or layer of a multilayer device can be in a range that is no larger than $1 \text{ m}^3$, $10 \text{ cm}^3$, $1 \text{ cm}^3$, $100 \text{ mm}^3$, $10 \text{ mm}^3$, $1 \text{ mm}^3$, $100 \text{ }\mu\text{m}^3$, $10 \text{ }\mu\text{m}^3$, $1 \text{ }\mu\text{m}^3$, or smaller.

A multilayer device of the present disclosure can be useful for transferring, storing, modifying, reacting or directing fluids. As such, multilayer fluidic devices are provided. The fluidic devices can include, for example, channels, reservoirs, inlets, outlets, chambers or other structural features that allow fluidic operation. These structural features can be configured and dimensioned to allow processing or storage of fluids on any of a variety of volume levels. For example, the features can have dimensions that contain no more than about 1, 10, or 100 picoliters; 1, 10, or 100 nanoliters; 1, 10, or 100 microliters; 1, 10, or 100 milliliters, or 1, 10, or 100 liters. In several embodiments, such as those demonstrated in the Examples section below, the dimensions of the fluidic features are determined by the size and shape of a spacer used on a solid support or sandwiched between two solid supports. For example, as demonstrated by the flowcell shown in FIG. 2, the volume of the flowcell channels is determined by the thickness of the black polyimide spacer and by the width of the cutout regions in the spacer.

In particular embodiments, an inorganic solid support and an organic solid support are brought into contact, wherein a radiation-absorbing material is present at the interface between them; and compression is applied at the interface while irradiating the radiation-absorbing material. This results in bonding between the inorganic solid support and the organic solid support to form a multilayer device. An inorganic solid support that is used in a method or device set forth herein can be made from any of a variety of materials including, but not limited to glass, silicon, metals (e.g. oxides of titanium, tin, nickel, zirconium or aluminum), fused silica, quartz, silicone (e.g. PDMS) or derivatives thereof or other materials set forth elsewhere herein or known in the art. An inorganic support can be made of a relatively homogenous material, for example, having no more than trace amounts of impurities. Alternatively, an inorganic support can include a heterogeneous material. For example, the inorganic support can include layers of different composition or features of different composition. Specific examples are glass substrates having an inner layer of metal (e.g. ITO), or discrete metal (e.g. ITO) features on the surface.

Other electrically conductive materials besides metals can be used. As set forth in the Examples section below, solid supports having electrically conductive layers or features are useful for electrical manipulation or detection of samples. ITO features (or other electrically conductive features) can be present on the surface of a solid support, for example, at locations that correspond to fluidic channels. The electrically conductive features can be absent from surface areas of a solid support (e.g. a glass slide) that bond to a second solid support (e.g. a polyimide spacer).

A solid support can include an array of features that are useful for analytical evaluation of nucleic acids or other analytes. The features can be present during one or more of the fabrication steps set forth herein, but are typically added at the later steps. For example, it may be desirable to add analytes, such as nucleic acids and/or surface features to which the analytes will attach, to a solid support after bonding has occurred between an organic solid support and inorganic solid support in order to avoid exposing the analyte and/or feature to harsh conditions such as laser irradiation, chemical bonding reagents, heat or pressure. The features of an array can be present in any of a variety of desired formats. For example, the features can be wells, pits, channels, ridges, raised regions, pegs, posts or the like. Optionally, the sites can contain beads. However, in particular embodiments the sites need not contain a bead or particle. Exemplary sites include wells that are present in substrates used for commercial sequencing platforms sold by 454 LifeSciences (a subsidiary of Roche, Basel Switzerland) or Ion Torrent (a subsidiary of Life Technologies, Carlsbad Calif.). Other solid supports having wells include, for example, etched fiber optics and other substrates described in U.S. Pat. Nos. 6,266,459; 6,355,431; 6,770,441; 6,859,570; 6,210,891; 6,258,568; 6,274,320; US 2009/0026082 A1; US 2009/0127589 A1; US 2010/0137143 A1; US 2010/0282617 A1 or PCT Publication No. WO 00/63437, each of which is incorporated herein by reference. In several cases the substrates are exemplified in these references for applications that use beads in the wells. The well-containing substrates can be used with or without beads in the methods or compositions of the present disclosure. In some embodiments, wells of a substrate can include gel material (with or without beads) as set forth in U.S. patent application Ser. No. 13/787,396, which is incorporated herein by reference.

The sites of an array can be metal features on an inorganic solid support (or other solid support). Metal can be deposited on a surface using methods known in the art such as wet plasma etching, dry plasma etching, atomic layer deposition, ion beam etching, chemical vapor deposition, vacuum sputtering, e-beam evaporation or sputtering or the like. Exemplary methods for depositing metals, for example, to create an array of metal features are provided in U.S. Ser. Nos. 13/783,043 and 13/492,661, each of which is incorporated herein by reference.

An array of features can appear as a grid of spots or patches. The features can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features. In particular embodiments, features of an array can each have an area that is larger than about 100 nm$^2$, 1 µm$^2$, 10 µm$^2$, 100 µm$^2$, or 500 m$^2$. Alternatively or additionally, features of an array can each have an area that is smaller than about 1 mm$^2$, 500 µm$^2$, 100 µm$^2$, 10 µm$^2$, 1 µm$^2$, or 100 nm$^2$.

For embodiments that include an array of features on a surface, such as the surface of an inorganic solid support, the features can be discrete, being separated by interstitial regions. The size of the features and/or spacing between the regions can vary such that arrays can be high density, medium density or lower density. High density arrays are characterized as having regions separated by less than about 15 m. Medium density arrays have regions separated by about 15 to 30 µm, while low density arrays have regions separated by greater than 30 µm. An array useful in the invention can have regions that are separated by less than 100 µm, 50 µm, 10 µm, 5 µm, 1 µm or 0.5 µm. Such density ranges can apply to arrays having an ordered pattern of features or arrays having a random pattern of features.

In particular embodiments, an array can include a collection of beads or other particles. Examples of arrays having beads located on a surface include those wherein beads are located in wells such as a BeadChip array (Illumina Inc., San Diego Calif.) or substrates used in sequencing platforms from 454 LifeSciences (a subsidiary of Roche, Basel Switzerland) or Ion Torrent (a subsidiary of Life Technologies, Carlsbad Calif.). Other arrays having beads located on a surface are described in U.S. Pat. Nos. 6,266,459; 6,355,431; 6,770,441; 6,859,570; 6,210,891; 6,258,568; 6,274,320; US 2009/0026082 A1; US 2009/0127589 A1; US 2010/0137143 A1; US 2010/0282617 A1 or PCT Publication No. WO 00/63437, each of which is incorporated herein by reference. Such surface configurations can be used on solid phase supports used in the devices set forth herein. Beads and/or wells can be present in a solid support prior to use in a support bonding method set forth herein. Alternatively, beads and/or wells can be added to a solid support during or after use in a support bonding method set forth herein.

Any of a variety of materials can be used as an organic solid support in a method or composition set forth herein including, but not limited to a polymer, thermoplastic, thermoset, cyclic olefin copolymer (COC), cyclic olefin polymer (COP), polyimide, polycarbonate, polyacrylic, Kapton, polyether ether ketone (PEEK) or derivatives thereof or other materials set forth herein. An organic solid support can be flexible or rigid as desired for particular uses. The methods set forth herein are particularly advantageous when used with a rigid inorganic solid support and a rigid organic support. Although not wishing to be bound by theory it is believed that the methods allow melting of one or both rigid supports to provide for closer contact to facilitate covalent bonding between the two rigid support materials. Melting one or both of the solid supports at an interface can be useful whether covalent bonds or non-covalent interactions result. The resulting bond is advantageous in preventing leakage. The bonding layer can form a seal to contain fluid, liquid or gas, or to direct flow of a liquid, fluid or gas.

An organic solid support can be made from a material that absorbs radiation in a region of the spectrum that corresponds with emission from a particular laser. For example, polyimide polymers such as Kapton polymers (DuPont) have absorption edges such that they absorb appreciably at wavelengths below about 650 nm. Thus, the Kaptons can be heated by radiation in this wavelength range, for example, from a laser that emits at 480 nm. Alternatively an organic solid support can be impregnated with a radiation absorptive material, or it can be coated with a radiation absorptive material. For example, an organic solid support can be impregnated or coated with a dye or with carbon black as is the case for black Kapton (carbon black-impregnated polyimide available from DuPont). A dye that is used can be matched to a particular laser according to overlap between the wavelength emitted by the laser and the absorption spectrum for the dye. A laser that emits at or close to peak absorption for a chosen dye is advantageous, but not necessary since off-peak absorption can be sufficient to achieve a desired level of bonding in embodiments of the methods set forth herein. As set forth in the Examples section below, black Kapton can be activated (e.g. via heating) by a laser that emits at 1064 nm.

Accordingly, an organic solid support that is present in a method or device set forth herein can absorb radiation in a part of the spectrum that matches a laser that is used in a bonding step. The organic solid support can absorb radiation in any of a variety of regions of the spectrum including for example in the UV (e.g. extreme UV or near UV), VIS (e.g. red, orange, yellow, green, blue, indigo or violet), or IR (e.g. near IR, mid IR or far IR) regions of the spectrum. It will be understood that an organic solid support can be chosen based on absence of absorption in one or more of regions of the spectrum, including for example, one or more of the aforementioned regions. In some embodiments, the inorganic solid support will transmit radiation in at least part of the spectrum that is absorbed by the organic solid support.

Although the methods have been exemplified above for embodiments wherein the organic sold support absorbs radiation that causes bonding at an interface between the organic solid support and an inorganic solid support, it will be understood that alternatively or additionally the inorganic solid support can be made from a material that absorbs the laser radiation. For example, the inorganic solid support can be impregnated with a radiation absorptive material, or it can be coated with a radiation absorptive material. Furthermore, a radiation absorbing material can be a liquid or other material that is present between an inorganic solid support and an organic solid support during or after bonding of a multilayer support. Such materials can be chosen based on ability to absorb radiation in any of a variety of regions of the spectrum including for example in the UV (e.g. extreme UV or near UV), VIS (e.g. red, orange, yellow, green, blue, indigo or violet), or IR (e.g. near IR, mid IR or far IR) regions of the spectrum. The material can be chosen based on absence of absorption in one or more of regions of the spectrum, including for example, one or more of the aforementioned regions. In some embodiments, the inorganic solid support will transmit radiation in at least part of the spectrum that is absorbed by the radiation absorbing material.

In particular embodiments, a chemically reactive layer will be present between an inorganic solid support and an organic solid support during a bonding step. The chemically reactive layer can be a coating on either or both of the organic solid support and inorganic solid support. Alternatively, the chemically reactive layer can be present in or on an intermediate material that is present between the two solid supports such that the two solid supports become attached via the intermediate material as a result of carrying out the fabrication method. Similarly, the chemically reactive layer can be a fluid layer containing cross-linking reagents that are reactive to both the organic solid support and the inorganic solid support.

A chemically reactive layer can be created on a solid support using, for example, a silanization method. Techniques such as vapor phase deposition, dip coating, spin coating and spray coating can be used to silanize a surface. In some embodiments, such methods can be used to apply a silane coat across the entirety of a surface. However, it is also possible to create a silanization pattern on a surface, for example, using masking methods or precision spraying methods. For example, as set forth in further detail below it may be desirable to apply silane (or other chemically reactive moieties) selectively to regions on the surface of an inorganic solid support that are to be bonded to an organic solid support, while avoiding or minimizing silanization (or other chemical modification) of other regions of the inorganic solid support where a bond to the organic slid support is not wanted. If desired the surface of an organic solid support can be patterned with silane or other chemically reactive coating using similar techniques.

Examples of silanes that can be used include, but are not limited to, acrylate functional silanes, aldehyde functional silanes, amino functional silanes, anhydride functional silanes, azide functional silanes, carboxylate functional silanes, phosphonate functional silanes, sulfonate functional silanes, epoxy functional silanes, ester functional silanes, vinyl functional silanes, olefin functional silanes, halogen functional silanes and dipodal silanes with any or none of the above functional groups. The choice of silane functionality can be made based on the reactivity of the organic material to which it will react. For example, amino functional silanes react with thermoplastics such as polyacrylate, polyamide, polyamide-imide, polybutylene terephthalate, polycarbonate, polyether ketone, polyethylene, polyphenylene sulfide, polysulfone, polyvinyl butyral and polyvinyl chloride. Vinyl and olefin functional silanes react with thermoplastics such as polyacetal, polyethylene, and polypropylene. Acrylate functional silanes react with thermoplastics such as polypropylene, and polystyrene.

A method of the present disclosure can include a step of irradiating a radiation-absorbing material that is present between an inorganic solid support and an organic solid support, thereby bonding the inorganic solid support and the organic solid support. The irradiation is typically carried out by a laser, but other radiation sources can be used if desired. A laser or other radiation source can be selected based on the wavelength and power of the radiation output that will produce desired bonding. Typically a wavelength is chosen that it transmits well through the transparent solid support and absorbs well in the radiation absorbing material. With higher laser powers, faster scan speeds can be achieved. For example lasers having power output in the range of 6 W-30 W, wavelengths in the range of 1060-1070 nm, and scanning at a rate in the range of 400-4000 mm/s have been shown to form excellent bonds between inorganic solid supports and organic layers containing carbon black. For example, in several embodiments the laser will be used to irradiate the absorbing material to cause sufficient heating to melt the inorganic layer or the organic layer.

Generally the radiation beam contacts the radiation absorbing material and is scanned along a path that delineates the desired bonding pattern at the interface of two solid supports. An example is shown in Panel A of FIG. 1, where a laser beam is directed orthogonal to the plane formed by the interface of the glass and polyimide spacer. Scanning the laser from edge to edge along the plane will produce a linear bonding layer that runs from one edge to the other. By extrapolating the diagram in Panel A of FIG. 1 to a 3 dimensional configuration it will be apparent that the laser can be scanned in a raster pattern in the same plane (i.e. from edge to edge and also in and out of the page a distance d) to produce a bonding pattern that runs from edge to edge and has a width d. Turning to the flowcell layers shown in FIG. 2 as an example, a laser can be scanned along the plane formed by the interface of the black polyimide and the glass to create a bonding layer. The path of the laser can correlate with the pattern of the black polyimide such that cutout regions (that form the channels) are avoided while other regions where black polyimide is in contact with the glass are irradiated. Although the method is exemplified with a laser that contacts the organic layer on the face that is in direct contact with the layer of the inorganic layer to which it will bond, it will be understood that irradiation can occur on the opposite side of the organic layer and heat can be transferred to the bonding face so long as a sufficiently thin organic layer is used.

An advantage of the laser bonding technique as that localized heating produces a bonding layer without causing substantial deformation of the solid supports. In contrast, other techniques that do not provide spatial discrimination when heating a spacer to the point of melting typically result in deformation of the spacer, which in turn deforms the shape of channels or other features in the spacer.

To achieve bonding in the methods of the present disclosure, the irradiation can pass through the inorganic solid support to contact the interface with the organic layer. As exemplified in Panel A of FIG. 1, the radiation from the laser passes through the upper glass support to contact the upper surface of the black polyimide spacer. The radiation beam is shown orthogonal to the plane of the interface in the figure, but in this or other embodiments the radiation beam can impinge at an angle with respect to the interface plane. Impinging at an angle can be beneficial when creating certain bonding patterns or to avoid features present on the inorganic solid support or on the organic solid support. Although not explicitly diagrammed in the static image shown in Panel A of FIG. 1, the lower glass support can be bonded to the black polyimide spacer by passing the laser beam through the lower glass substrate to irradiate the interface between the black polyimide spacer and the lower glass support. Thus, both of the glass substrates can be bonded to opposite surfaces of the black polyimide layer to form the multilayer device.

Figure 1:
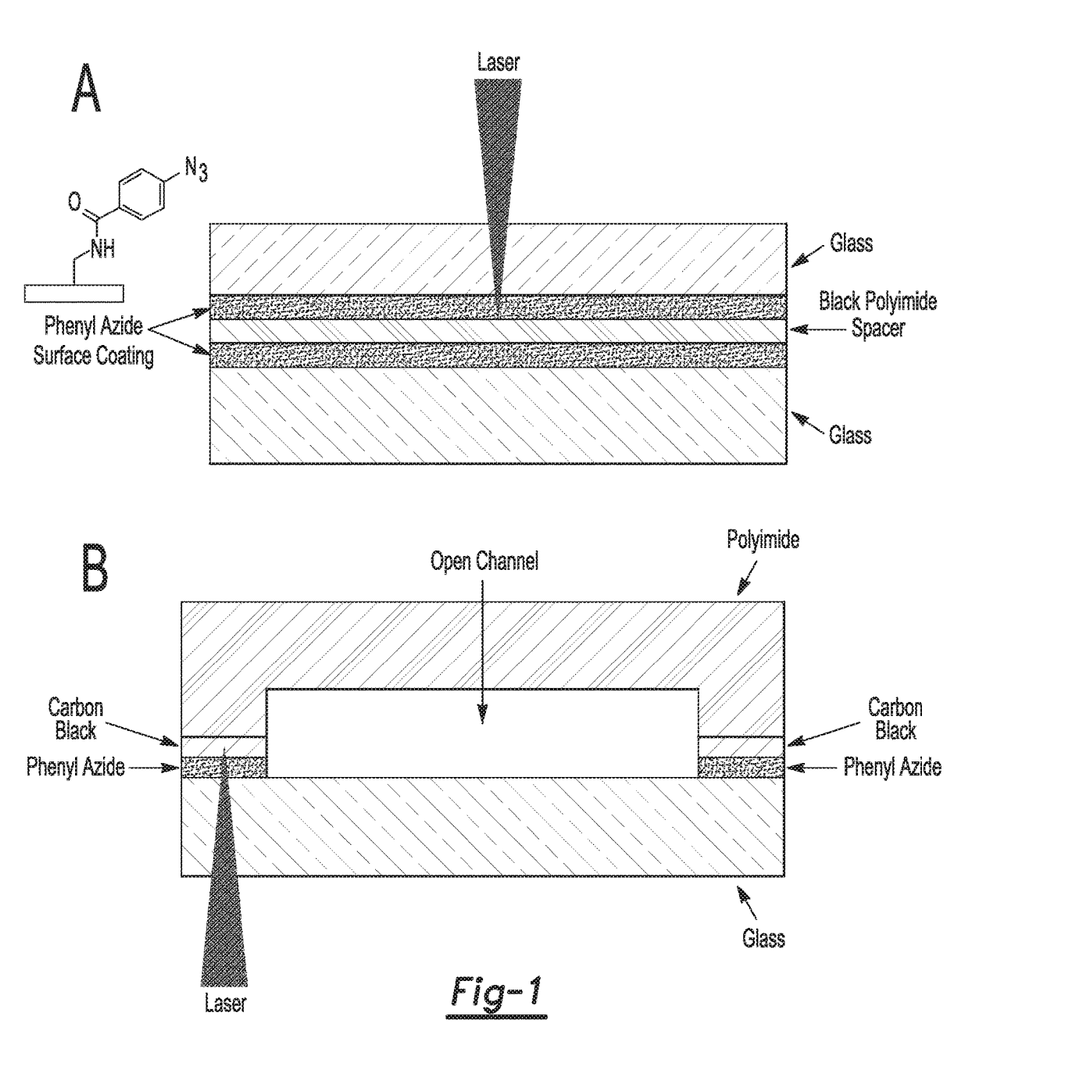
FIG. 1 shows profile views of multilayer fluidic devices undergoing a laser induced bonding process, wherein Panel A shows a device formed by an organic layer between two inorganic layers and Panel B shows a device formed by a single organic layer bonded to a single inorganic layer.

An alternative configuration is shown in Panel B of FIG. 1. Here the organic layer provides three sides to the channel (e.g. both the sidewalls and the top for the channel). In the diagram shown, the polyimide layer has laser bonding feet that are coated or locally impregnated with carbon black. Thus, the laser absorbing layer is present on the organic layer in a pattern that defines the channel footprint on the glass surface. In the example shown, the phenyl azide layer is also provided in a pattern that defines the footprint (optionally, the phenyl azide need not be patterned). Laser bonding of the components shown in Panel B of FIG. 1 will create a multilayer fluidic device having a single inorganic layer (e.g. glass) bonded to a single organic layer (e.g. polyimide), wherein the organic layer is shaped to provide all but one side of the channel (i.e. the side formed by the glass surface).

As set forth above, a pattern of bonding between an inorganic solid support and organic solid support can be created by selectively directing radiation in a pattern that delineates the bonding pattern. A pattern of bonding can also be delineated by the surface pattern of the organic solid support, the pattern of a chemically reactive layer at the interface of the inorganic and organic supports, and/or the surface pattern of the inorganic support. FIG. 2 shows an example where the surface pattern of an organic support delineates the bonding pattern. In this example, the radiation pattern can replicate the pattern of the organic support surface. However, the radiation pattern need not follow the pattern of the organic support in this example since the cutouts in the organic solid support prevent bonding at unwanted locations on the surface. This is also the case when using a pattern for the chemically reactive layer or a surface pattern for the inorganic support. Thus, a pattern of radiation can be optionally used in combination with a solid support surface pattern and/or a pattern of a chemically reactive layer.

Figure 6:
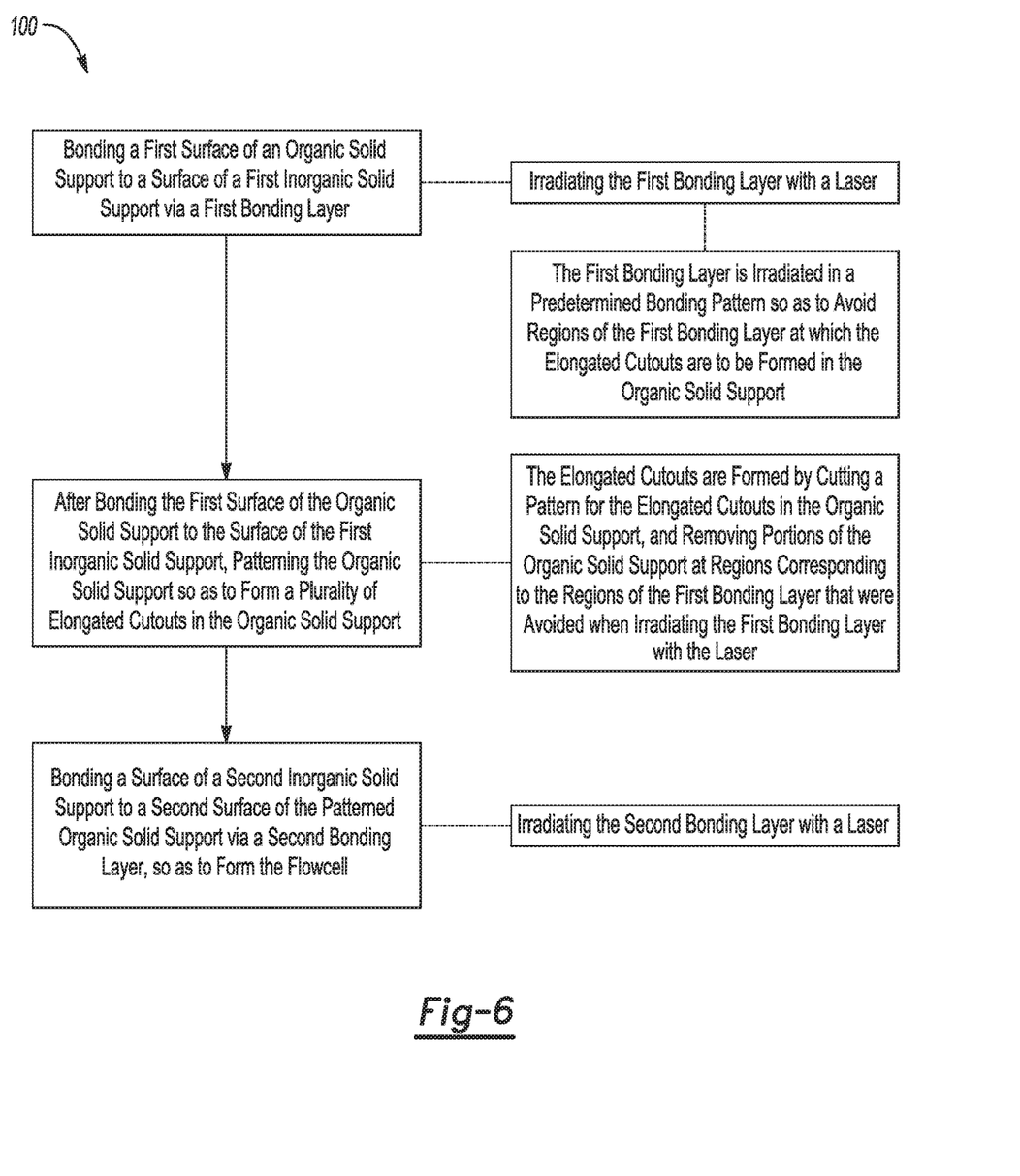
FIG. 6 is a flow diagram depicting an example method for making a multilayer device.

The organic solid support need not be patterned prior to formation of a bonding layer with an inorganic solid support. Rather, a pattern can be created by cutting the organic support after bonding has occurred. It is generally advantageous to use a selective radiation pattern, a pattern for the chemically reactive layer and/or a surface pattern for the inorganic support when the organic support is to be cut after bonding. Such patterning will allow for easier removal of the cut out area since it will not be attached to the inorganic support surface. Excess material can be removed by cutting away with a laser tuned to a wavelength with significant absorption in the spacer material, or with a blade-based cutter/plotter. An example of this method (reference numeral 100) is shown in FIG. 6.

The present disclosure provides a fluidic device made, for example, by the methods set forth above. For example, the present disclosure provides a fluidic device having at least one channel defined by an inorganic solid support attached to an organic solid support by a bonding layer, wherein the fluidic device is made by the process of: (a) contacting the inorganic solid support, the organic solid support and a radiation-absorbing material in a configuration wherein the radiation-absorbing material is present at an interface between the inorganic solid support and the organic solid support; and (b) applying compression at the interface and irradiating the radiation-absorbing material with the radiation to form the bonding layer between the inorganic solid support and the organic solid support. In particular embodiments, the radiation-absorbing material is not an electrically conductive material such as a metal.

A fluidic device of the present disclosure, whether or not it is made by the methods exemplified herein can include features and characteristics of the multilayer devices made by such methods. In particular embodiments, a fluidic device can include (a) an inorganic solid support attached to an organic solid support by a bonding layer, wherein the inorganic solid support has a rigid structure and wherein the bonding layer includes a material that absorbs radiation at a wavelength that is transmitted by the inorganic solid support or the organic solid support, and (b) at least one channel formed by the attachment of the inorganic solid support to the organic solid support, wherein the channel is configured to contain a liquid and the bonding layer that attaches the inorganic solid support to the organic solid support provides a seal against liquid flow. In particular embodiments, the material that absorbs radiation is not an electrically conductive material. For example, in some embodiments, the material that absorbs radiation is not a metal.

A fluidic device of the present disclosure is particularly useful for array analysis. For example, a fluidic device can contain an array having nucleic acid features. A particularly desirable use for the nucleic acid features is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. No. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference.

A nucleic acid array can also be used in a sequencing procedure, such as a sequencing-by-synthesis (SBS) technique. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Other sequencing procedures that use cyclic reactions can be used, such as pyrosequencing (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference), Sequencing-by-ligation (Shendure et al. *Science* 309:1728-1732 (2005); U.S. Pat. Nos. 5,599,675; and 5,750,341, each of which is incorporated herein by reference), sequencing-by-hybridization (Bains et al., *Journal of Theoretical Biology* 135(3), 303-7 (1988); Drmanac et al., *Nature Biotechnology* 16, 54-58 (1998); Fodor et al., *Science* 251 (4995), 767-773 (1995); and WO 1989/10977, each of which is incorporated herein by reference), FRET-based sequencing (Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference), or sequencing based on detection of released protons (US Pat. App. Pub. Nos. 2009/0026082 A1; 2009/0127589 A1; 2010/0137143 A1; or 2010/0282617 A1, each of which is incorporated herein by reference).

Other useful applications for an array of the present disclosure are gene expression analysis or genotyping analysis. Exemplary methods for array-based expression and genotyping analysis that can be carried out on an array of the present disclosure are described in U.S. Pat. No. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference. Gene expression and genotyping can also be performed using sequencing techniques.

The attachment of a nucleic acid to a feature can be via an intermediate structure such as a bead, particle or gel. Attachment via a gel is exemplified by flowcells available commercially from Illumina Inc. (San Diego, Calif.) or described in WO 2008/093098, which is incorporated herein by reference. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, U.S. patent application Ser. No. 13/784,368, which is incorporated herein by reference). Attachment via a bead can be achieved as exemplified in the description and cited references set forth previously herein.

In several embodiments, the surface of a fluidic device can include oligonucleotide primers used for capture and/or amplification of template nucleic acids. The primers can be present as a lawn on one or more surfaces of the device. Alternatively, the primers can be present at patterned features as described, for example, in U.S. patent application Ser. Nos. 13/492,661; 13/661,524; 13/783,043; and Ser. No. 13/787,396, each of which is incorporated herein by reference. The primers can be universal primers that hybridize to a universal adapter sequence that is attached to different target nucleic acids in a library (i.e. each target nucleic acid includes a target region that differs from other target nucleic acids in the library and several target nucleic acids in the library have the same universal adapter sequence). In some embodiments, a target nucleic acid can be solid-support-attached, and primers (whether in solution or also solid-support-attached) can be used to amplify the attached target nucleic acid (i.e. the target nucleic acid can serve as a template for amplification).

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be solid-support-attached. In PCR embodiments, one or both of the primers used for amplification can be solid-support-attached. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. PCR amplification can also be carried out with one of the amplification primers being solid-support-attached and the second primer being in solution. Exemplary components that can be used in an RCA reaction and principles by which RCA produces amplicons are described, for example, in Lizardi et al., *Nat. Genet.* 19:225-232 (1998) and US Pat. App. Pub. No. 2007/0099208 A1, each of which is incorporated herein by reference. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference.

The following examples are intended to illustrate but not limit the present invention.

Example I

Fabricating Flowcells

This example describes a method for fabricating a flowcell device by bonding a polyimide spacer between two planar glass supports. A layer that includes chemically reactive linkers and a radiation absorbing material is formed between the polyimide spacer and the glass. Laser activation of this layer results in bonding of the glass to the polyimide.

Diagrammatic representations of methods for fabricating a flowcell are shown in FIG. 1 and FIG. 2. A rectangular glass slide is coated on one side with (3-aminopropyl)-triethoxysilane (APTES) to form an amino silane layer and the amino group is reacted with N-Hydroxysuccinimidyl-4-azidosalicylic Acid (HSAB) to form a phenyl azide layer. A sheet of black Kapton (polymide containing carbon black from DuPont) having rectangular dimensions similar to the glass slide and a thickness of 100 microns is pre-patterned to contain cutouts for flowcell lanes. A spacer having cutouts for 6 lanes is exemplified in FIG. 2. The black Kapton spacer is exposed to oxygen plasma and then compressed against the glass slide with approximately 100 PSI of pressure while laser energy at 1064 nm wavelength is applied to the spacer. The laser spot can be scanned rapidly for higher power lasers (3500 mm/s for a 30 W laser) or more slowly to accommodate lower power laser systems (400 mm/s for a 6 W laser). Continuous wave (CW) mode lasers have an advantage of delivering even energy over time, but the process can be tuned to use pulse mode lasers as well.

The black Kapton spacer need not be pre-cut if the phenyl azide coating is patterned on the glass slide (i.e. silane reagents are present at the locations where spacer will attach to form the walls of the channels and are absent from the locations where spacer material will be removed to form the channels). Alternatively or additionally, the path of irradiation from the laser can follow the shape of the spacer such that bonding does not occur at the locations where spacer material will be subsequently cut out to form channels.

The resulting fluidic device will have several channels defined by the cutouts in the spacer and the glass bottom support. These open channels can be enclosed by bonding a second glass slide, having similar rectangular dimensions as the bottom glass slide, to the exposed side of the black Kapton spacer. The top glass slide is coated with the phenyl azide layer, the spacer is exposed to oxygen plasma, and the top glass slide is compressed against the spacer while laser energy at 1064 nm wavelength is applied to the black Kapton. One of the glass slides can be pre-drilled with ingress and egress apertures for the flowcell lanes (as exemplified in FIG. 2). Alternatively, the apertures can be drilled after bonding to the spacer.

As set forth above, a radiation absorbing material (e.g. carbon black) can be present in the polyimide spacer to allow it to absorb the laser energy which in turn leads to formation of the bond between the glass and spacer. Alternatively, a wavelength that is significantly absorbed by the natural polyimide material (e.g. 480 nm) can be used instead of adding carbon black or other radiation absorbing material to the spacer. As another example, polyimide CEN JP can be bonded when irradiated with light at 532 nm.

Without intending to be bound by theory, it is contemplated that the bond formed using the methods of this example, may differ from a traditional transmission laser weld where two materials melt and diffuse into one another across the interface. Rather, using the methods described in this example, the laser energy may be acting to soften one or both materials allowing for the contact required for a covalent bond to occur.

Example II

Fabricating Flowcells for Use in Electric Field Assisted Nucleic Acid Capture

This example demonstrates a cost-effective, metal-free bonding technique for flowcell assembly. An advantage of the technique is that metal, such as titanium which is often used to create a transmission laser weld, can be eliminated from flowcell fabrication. This can reduce the cost of materials for flowcell manufacture since titanium is relatively expensive. Avoiding metals such as titanium can also provide for a bond between the spacer and glass that is more robust for applications where an electrical current is passed through the flowcell; otherwise electrochemistry can occur at the bonding interface to weaken the structure of the flowcell.

Figure 3:
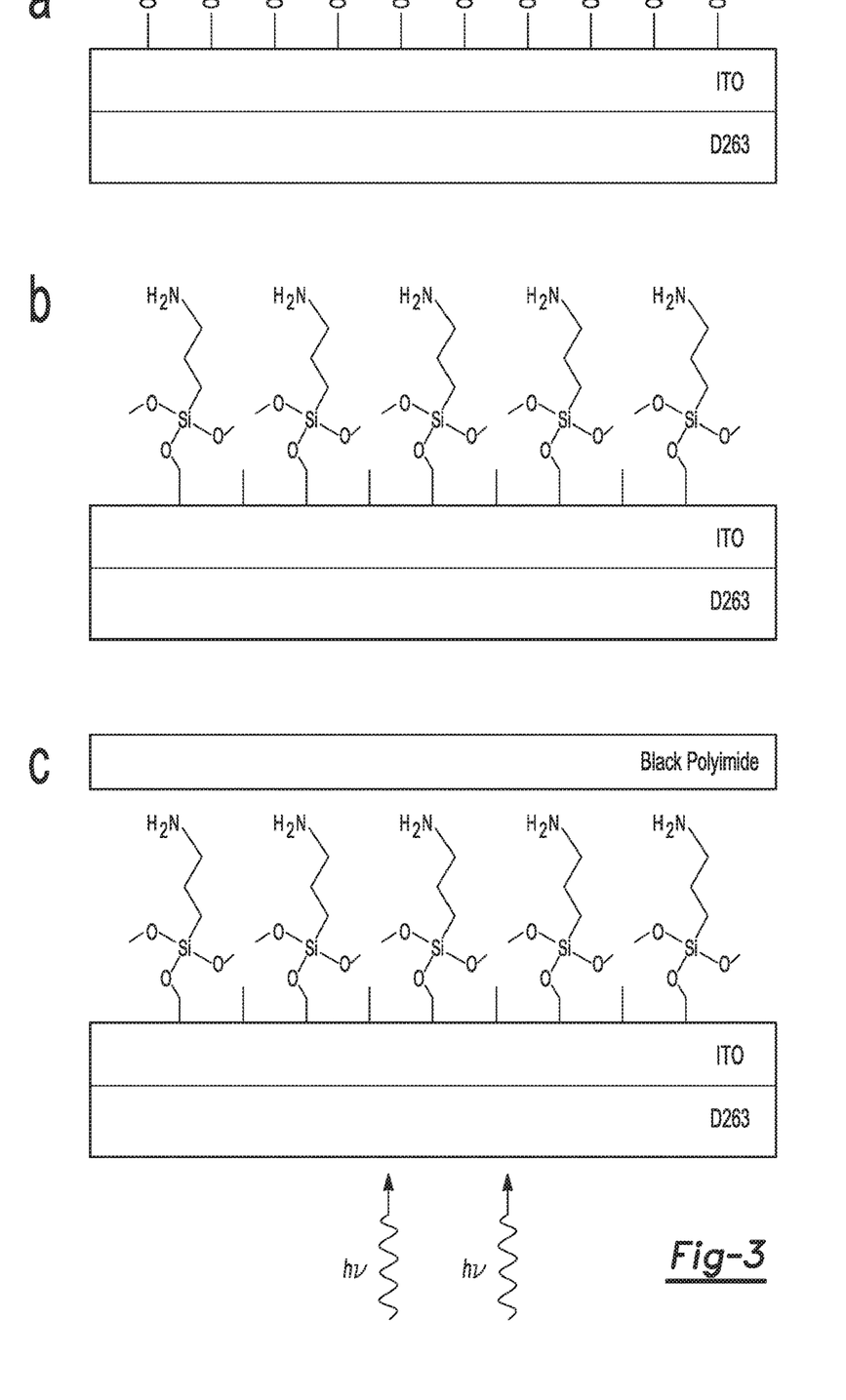
FIG. 3 shows (a) Activation of ITO on D263 surface using Oxygen plasma (b) Surface functionalization of ITO with APTMS and (c) IR bonding of black polyimide to silanized surface.

A diagrammatic representation of the bonding process is shown FIG. 3. Borosilicate thin glass (D263 glass) having an indium tin oxide (ITO) coating was treated with plasma to activate the ITO surface and enrich it with hydroxyl groups. Next a vapor phase silanization was done with (3-aminopropyl)-trimethoxysilane (APTMS) to covalently link surface —OH groups to the silane followed by a thermal bake step to completely crosslink the silane layer on the surface. The black Kapton (black polyimide) was then chemically bonded to the silanized surface using 1064 nm laser irradiation. Black polyimide absorbs strongly in the IR region of the spectrum and it is a thermoplastic. Although not wishing to be bound by theory it is believed that the heated polyimide reflows at the silane interface to form what appear to be covalent bonds. As demonstrated in Example III, peel strengths for the resulting bond are comparable or surpass measured values achieved using titanium welded bonds for the same materials.

The bonding process at the whole flowcell level occurred similarly to that shown in FIG. 2 (except that the surface coated glass included an ITO layer). More specifically, a black polyimide gasket was first UV laser cut with Cr/Au pads evaporated directly on the black polyimide. To promote the adhesion of Cr/Au to the polyimide, an $O_2$ plasma pre-treatment of the polyimide was performed. A Cr/Au thickness of above 150 nm was beneficial to formation of robust, low resistance contacts upon bonding to the silanized ITO layer and allowed storage in electrolyte for over 1 week without measurable degradation of the conductance. This technique allows for good electrical contact to the ITO with contact resistance <10 Ohms.

Figure 5:
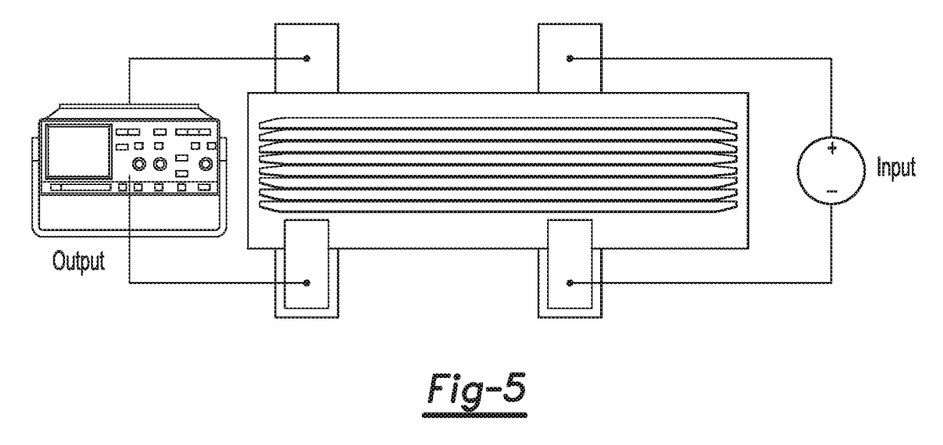
FIG. 5 shows a diagram in which input and output devices are electrically connected to pairs of electrical contacts of the flowcell of FIG. 4.

A photograph of a flowcell bonded using this technique is shown in FIG. 4. The flowcell offers two electrical contacts per ITO layer. As diagrammed in FIG. 5, this allows for an input potential/waveform to be applied across a pair of input electrodes and the same potential/waveform can be measured across the output electrodes ensuring minimal contact resistance.

To test the application of electric fields inside the flowcell, electric field assisted patterning was performed as set forth in U.S. patent application Ser. No. 13/783,043, which is incorporated herein by reference, with the following modifications. The electrodes were biased at 2V with $K_2SO_4$ filled in 4 of the flowcell lanes. A TET QC pre- and post E-field burnoff revealed that indeed oligonucleotide primers were removed (~60% reduction in primer intensity observed). Nucleic acid capture and amplification was carried out on various lanes of the flowcell. Patterned nucleic acid clusters were clearly visible, confirming that electric fields could be successfully applied in the flowcell using this technique.

To test the robustness of this flowcell bonding technique, 26 cycles of sequencing were successfully completed on the flowcell without fluid leakage or vacuum failures. Sequencing was carried out as set forth in U.S. patent application Ser. No. 13/783,043, which is incorporated herein by reference.

Example III

Testing Structural Characteristics of Flowcells

This example describes methods for evaluating structural characteristics of multilayer devices. This example also demonstrates advantageous features of flowcells produced by the methods set forth in Example II.
Peel Test One way to measure the bond strength between the glass and polyimide is to bond a test strip and then measure the force required to physically peel it off the glass. Typically a range of laser conditions are applied one per block down the length of a slide. The peel strip is then cut to a known width and length, and can be placed in the peel tester for measurement. The force applied to the grippers is measured approx 5 times a second to give a set of readings showing the peel strength of each of the welded strips. Typically, the peel strip is cut into two sections, so that either both can be peeled under the same conditions (better statistics) or one can be peeled after accelerated wet storage (to measure the robustness of the bond to storage).

The peel test was used to compare the strength of the bond formed between black Kapton and silanized glass in the presence or absence of laser treatment. Black Kapton films were uniformly treated as described in Example II and brought into contact with the glass under significant pressure (~100 PSI across the entire film). The glass was also treated as described in Example II. The laser was applied to selective areas of the two substrates (and not to other areas). Only those areas which were exposed to the laser formed a bonding layer. Non-lased areas remained completely non-bonded, despite having identical chemistry and being compressed together.

The peel test was also used to evaluate robustness of flowcells to storage in aqueous solution. Pairs of flowcells were produced by the methods described in Example II. Test flowcells were produced and stored in aqueous solution for 7 days at 80° C. prior to peel test. Control flowcells were produced and subjected to peel tests without prior storage in the aqueous solution. The results of the peel tests showed that storage did not adversely impact bonding strength for flowcells produced by the methods set forth in Example II.
Pressure Leak Test A flowcell was fabricated as described in Example II. Pressurized air/$N_2$ (at 30 PSI pressure) was then forced into all or some of the lanes through a gasketed pressure manifold. The rate at which the pressure decayed (due to air leaking out) was then monitored over 1 min. This is a non-destructive test, so the flowcell can be tested repeatedly over a succession of time points-typically with the flowcell being held in accelerated storage conditions between the tests. In this way, the quality of the initial bond and how long the flowcell can be stored without developing leaks can be evaluated.

Flowcells were produced as described in Example II and stored in aqueous solution at 80° C. for various time periods prior to being subjected to the pressure leak test. The flowcells were shown to last 20-30 days in these conditions without leaking (>90% of tested flowcells passing).

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of making a flowcell, the method comprising:
bonding a first surface of an organic solid support to a surface of a first inorganic solid support via a first bonding layer formed of a radiation-absorbing material, wherein the organic solid support includes a plurality of elongated cutouts; and
bonding a surface of a second inorganic solid support to a second surface of the organic solid support via a second bonding layer formed of the radiation-absorbing material, so as to form the flowcell;
wherein:
the formed flowcell comprises a plurality of channels defined by the surface of the first inorganic solid support, the surface of the second inorganic solid support, and walls of the elongated cutouts;
prior to bonding the first surface of the organic solid support to the surface of the first inorganic solid support, the method further comprises:
coating the surface of the first inorganic solid support with (3-aminopropyl)-triethoxysilane (APTES) to form an amino silane layer; and
reacting amino groups of the amino silane layer with N-Hydroxysuccinimidyl-4-azidosalicylic Acid (HSAB) to form a phenyl azide layer; and
wherein prior to bonding the surface of the second inorganic solid support to the second surface of the organic solid support, the method further comprises:
coating the surface of the second inorganic solid support with (3-aminopropyl)-triethoxysilane (APTES) to form a second amino silane layer; and reacting amino groups of the second amino silane layer with N-Hydroxysuccinimidyl-4-azidosalicylic Acid (HSAB) to form a second phenyl azide layer.

2. The method of claim 1, wherein:
bonding the first surface of the organic solid support to the surface of the first inorganic solid support comprises irradiating the first bonding layer with a laser; and
bonding the surface of the second inorganic solid support to the second surface of the organic solid support comprises irradiating the second bonding layer with the laser.

3. The method of claim 2, wherein:
in irradiating the first bonding layer with the laser, the first bonding layer is irradiated in a predetermined bonding pattern so as to avoid regions of the first bonding layer corresponding to the elongated cutouts of the organic solid support; and
in irradiating the second bonding layer with the laser, the second bonding layer is irradiated in a predetermined bonding pattern so as to avoid regions of the second bonding layer corresponding to the elongated cutouts of the organic solid support.

4. The method of claim 2, wherein the organic solid support comprises a polyimide that contains carbon black, and wherein each of the polyimide and the carbon black absorbs radiation emitted by the laser used in the bonding.

5. The method of claim 1, wherein each of the first and second inorganic solid supports is made of silica or a silica-based material.

6. The method of claim 1, wherein each of the first and second inorganic solid supports comprises a plurality of wells, and each well contains a gel material.

7. A method of making a flowcell, the method comprising:
bonding a first surface of an organic solid support to a surface of a first inorganic solid support via a first bonding layer, wherein the organic solid support includes a plurality of elongated cutouts;
bonding a surface of a second inorganic solid support to a second surface of the organic solid support via a second bonding layer, so as to form the flowcell;
wherein the formed flowcell comprises a plurality of channels defined by the surface of the first inorganic solid support, the surface of the second inorganic solid support, and walls of the elongated cutouts;
and wherein each of the first and second inorganic solid supports comprises a plurality of wells, and each well contains a gel material that comprises a poly(N-(5-azidoacetamidylpentyl)acrylamide-co-acrylamide (PAZAM) polymer.

8. A method of making a flowcell, the method comprising:
bonding a first surface of an organic solid support to a surface of a first inorganic solid support via a first bonding layer;
after bonding the first surface of the organic solid support to the surface of the first inorganic solid support, patterning the organic solid support so as to form a patterned organic solid support including a plurality of elongated cutouts in the organic solid support; and
bonding a surface of a second inorganic solid support to a second surface of the patterned organic solid support via a second bonding layer, so as to form the flowcell;
wherein the formed flowcell comprises a plurality of channels defined by the surface of the first inorganic solid support, the surface of the second inorganic solid support, and walls of the elongated cutouts.

9. The method of claim 8, wherein:
each of the first and second bonding layers is formed of a radiation-absorbing material;
bonding the first surface of the organic solid support to the surface of the first inorganic solid support comprises irradiating the first bonding layer with a laser; and
bonding the surface of the second inorganic solid support to the second surface of the patterned organic solid support comprises irradiating the second bonding layer with the laser.

10. The method of claim 9, wherein:
in irradiating the first bonding layer with the laser, the first bonding layer is irradiated in a predetermined bonding pattern so as to avoid regions of the first bonding layer at which the elongated cutouts are to be formed in the organic solid support;
in patterning the organic solid support, the elongated cutouts are formed by cutting a pattern for the elongated cutouts in the organic solid support, and removing portions of the organic solid support at regions corresponding to the regions of the first bonding layer that were avoided when irradiating the first bonding layer with the laser.

11. The method of claim 8, wherein each of the first and second inorganic solid supports is made of silica or a silica-based material.

12. The method of claim 8, wherein:
bonding the first surface of the organic solid support to the surface of the first inorganic solid support comprises irradiating the first bonding layer with a laser;
bonding the surface of the second inorganic solid support to the second surface of the organic solid support comprises irradiating the second bonding layer with the laser; and
the organic solid support comprises a polyimide that contains carbon black, and each of the polyimide and the carbon black absorbs radiation emitted by the laser.

13. The method of claim 8, wherein each of the inorganic solid supports comprises a plurality of wells, and each well contains a gel material.

14. A method of making a flowcell, the method comprising:
bonding a first surface of an organic solid support to a surface of a first inorganic solid support via a first bonding layer;
after bonding the first surface of the organic solid support to the surface of the first inorganic solid support, patterning the organic solid support so as to form a plurality of elongated cutouts in the organic solid support;
bonding a surface of a second inorganic solid support to a second surface of the patterned organic solid support via a second bonding layer, so as to form the flowcell;
wherein the formed flowcell comprises a plurality of channels defined by the surface of the first inorganic solid support, the surface of the second inorganic solid support, and walls of the elongated cutouts;
and wherein each of the inorganic solid supports comprises a plurality of wells, and each well contains a gel material comprising a poly(N-(5-azidoacetamidylpentyl)acrylamide-co-acrylamide (PAZAM) polymer.

15. A flowcell comprising:
a first inorganic solid support;
a second inorganic solid support;
an organic solid support, wherein the organic solid support includes a plurality of elongated cutouts;

a first bonding layer bonding a first surface of the organic solid support to a surface of the first inorganic solid support, wherein the first bonding layer comprises a first chemically reactive layer of a silane or phenyl azide; and a second bonding layer bonding a surface of the second inorganic solid support to a second surface of the organic solid support, wherein the second bonding layer comprises a second chemically reactive layer of the silane or phenyl azide;

wherein the organic solid support includes a radiation-absorbing material;

wherein the flowcell comprises a plurality of channels defined by the surface of the first inorganic solid support, the surface of the second inorganic solid support, and walls of the elongated cutouts.

16. The flowcell of claim 15, wherein:

each of the first and second inorganic solid supports is made of silica or a silica-based material;

and the radiation-absorbing material comprises a polyimide that contains carbon black.

17. The flowcell of claim 15, wherein each of the inorganic solid supports comprises a plurality of wells, and each well contains a gel material.

18. A flowcell comprising:

a first inorganic solid support;

a second inorganic solid support;

an organic solid support, wherein the organic solid support includes a plurality of elongated cutouts;

a first bonding layer bonding a first surface of the organic solid support to a surface of the first inorganic solid support; and a second bonding layer bonding a surface of the second inorganic solid support to a second surface of the organic solid support;

wherein the flowcell comprises a plurality of channels defined by the surface of the first inorganic solid support, the surface of the second inorganic solid support, and walls of the elongated cutouts;

and wherein each of the inorganic solid supports comprises a plurality of wells, and each well contains a gel material comprising a poly(N-(5-azidoacetamidylpentyl)acrylamide-co-acrylamide (PAZAM) polymer.

19. A method of making a flowcell, the method comprising:

bonding a first surface of an organic solid support to a surface of a first inorganic solid support via a first bonding layer formed of a radiation-absorbing material, wherein the organic solid support includes a plurality of elongated cutouts; and bonding a surface of a second inorganic solid support to a second surface of the organic solid support via a second bonding layer formed of the radiation-absorbing material, so as to form the flowcell;

wherein:

the formed flowcell comprises a plurality of channels defined by the surface of the first inorganic solid support, the surface of the second inorganic solid support, and walls of the elongated cutouts;

prior to bonding the first surface of the organic solid support to the surface of the first inorganic solid support, the method further comprises:

coating the surface of the first inorganic solid support with indium tin oxide;

plasma treating the indium tin oxide to enrich it with hydroxyl groups;

performing a vapor phase silanization with (3-aminopropyl)-trimethoxysilane to covalently link the hydroxyl groups to the (3-aminopropyl)-trimethoxysilane to form a silane layer; and baking to crosslink the silane layer;

prior to bonding the surface of the second inorganic solid support to the second surface of the organic solid support, the method further comprises:

coating the surface of the second inorganic solid support with indium tin oxide;

plasma treating the indium tin oxide to enrich it with hydroxyl groups;

performing a vapor phase silanization with (3-aminopropyl)-trimethoxysilane to covalently link the hydroxyl groups to the (3-aminopropyl)-trimethoxysilane to form a second silane layer; and baking to crosslink the second silane layer.

* * * * *

UNITED STATES PATENT AND TRADEMARK OFFICE
CERTIFICATE OF CORRECTION

PATENT NO. : 11,110,452 B2
APPLICATION NO. : 16/026847
DATED : September 7, 2021
INVENTOR(S) : Jeffrey S. Fisher, John A. Moon and Bali Murali Venkatesan It is certified that error appears in the above-identified patent and that said Letters Patent is hereby corrected as shown below:

In the Claims

Column 19, Line 27:
In Claim 4, delete "laser used in the bonding." and insert -- laser. --, therefor.

Signed and Sealed this
Tenth Day of May, 2022

Katherine Kelly Vidal
*Director of the United States Patent and Trademark Office*